US00PP09601P

United States Patent [19]

Ott

[11] Patent Number: Plant 9,601

[45] Date of Patent: Jul. 9, 1996

[54] 'RED AND WHITE' POINSETTIA

[76] Inventor: Cleveland Ott, 677 Grater Ave., Graterford, Pa. 19426

[21] Appl. No.: 368,272

[22] Filed: Dec. 1, 1994

[51] Int. Cl.[6] ..... A01H 5/00

[52] U.S. Cl. ..... Plt./86.1

[58] Field of Search ..... Plt./86.1, 86.2, Plt./86.3, 86.4

[56] References Cited

U.S. PATENT DOCUMENTS

P.P. 3,889 5/1976 Fantom ..... Plt./86.1

P.P. 7,234 5/1990 Fruehwirth ..... Plt./86.1

*Primary Examiner*—James R. Feyrer

*Attorney, Agent, or Firm*—Joseph W. Molasky & Associates

[57] ABSTRACT

A new variety of poinsettia in which the bract coloration is distinctly red with distinct white mottling. This plant was found among Angelika White cultivars, and it shares with them a similar leaf color, height, and blooming habit.

1 Drawing Sheet

PREAMBLE

This relates to a new Pointsettia which is distinguishable from other poinsettias by its red and white mix of colors.

Each bract differs from every other bract, but all have in common a variegated appearance characterized by a mix of distinct red and distinct white.

BACKGROUND OF THE INVENTION

When first discovered by J. R. Poinsett in Mexico in 1828, the poinsettia was noted for its vivid coloration which varied between scarlet, pink, and white; however, it has since demonstrated a unique ability to mutate, and horticulturists have produced from this member of the Spurge family a wide variety of new cultivars.

In 1976, John Fantom was issued a patent to a Poinsettia having variegated red and pink bracts (U.S. Plant Pat. No. 3,889). In this cultivar, the bracts are brick red and the pink is in the form of spots and blotches.

Variations on this red-pink theme are also covered by F. Fruehwirth in patents which claim a dark red and light pink coloration (U.S. Plant Pat. No. 7,308), red with pink flecks (U.S. Plant Pat. No. 7,230), and "bi-colored red and pink" (U.S. Plant Pat. No. 8,771).

To the discoverer's knowledge, there has not previously been patented a cultivar of Poinsettia which has solely red and white bract colors and the other characteristics of the plant of this disclosure and one lacking pink bract shades as the plant herein disclosed.

It is anticipated that the plant of this discovery will be sold under the trademark SAN-T-CLAUS.

ORIGIN

The present cultivar was found, by Applicant, in his greenhouse in Graterford, Pa. on Dec. 3, 1993.

Applicant does not profess to know the precise origin of this plant, but it was discovered by him in a bench among Angelika White cultivars. Other varieties may also have been present.

About 400 of these specimens have been reproduced to date. None have been sold.

THE PHOTOGRAPH

The Poinsettia of this invention is known botanically as *Euphorbia pulcherrima*. The accompany photo shows a top view of a typical plant in full bloom. Color descriptions are made in accordance with the *Royal Horticultural Society Colour Chart*, except where color descriptions of ordinary meaning are appropriate.

BRIEF DESCRIPTION

The plant of this discovery has essentially the same plant characteristics and growing habit as its suspected parent 'Angelika', but differs therefrom primarily in the coloration expressed in the leaf and bract petioles and in bract coloration. The plant is distinguished from the suspected parent plant by having bracts which are of distinctly red and white coloration, which are variegated with the bract laminas being predominantly red having blotches of white coloration. On the Horticultural Color Chart, it is #53-B, Cardinal Red (the British Color Council identifies #53-B as Cardinal).

The characteristics of this new cultivar are based on observations made of flowering plants grown in Applicant's greenhouses in Graterford, Pa.

This new plant is particularly distinguished in having a characteristic, nonuniform expression of white spots or mottles in its predominantly red bract color. The white spots or mottles are characteristically not uniform in size and expressed in widely varying ranges of paterns and locations of white spots. This plant is believed to be a stabilized chimera and is easily maintained by the prudent selection of stock material for asexual reproduction which does not express an extreme of white or red in the bract coloration.

There is no difficulty in selecting cuttings because the colors are clearly visible, and one has only to look to the color of the leaf petiole during harvesting. The leaf petiole will be green and red, the same as the variegated bract.

After selection, the plants are reproduced asexually from rooted cuttings for propagation purposes. The selected plant is stable and has been repeatedly asexually reproduced by the inventor or under his direction by rooting cuttings at the above noted location. Rooting is superior to those of almost all known Poinsettia varieties.

Propagation over successive generations has demonstrated that the red and white coloration of this cultivar is true and consistently reproducible.

The color patterns vary considerably so that no two are ever the same, but all of the bracts have in common a unique variegated coloration consisting of distinct red with distinct white mottling.

DETAILED DESCRIPTION

Classification:

*Botanic.*—*Euphorbia pulcherrima.*

*Varietal.*—Red and White.

*Common name.*—Poinsettia.

Foliage: The leaves are typically ovate, and at maturity, they about 12–15 cm long and about 8–10 cm wide. The foliage is clean and uniformly green from top to bottom. Leaf retention is good even at room temperature under low light intensity.

Cyathia: Each cyanthium is green with yellow nectar cups, and fringed with red at the distal end. In general, about 12–20 cyathia can be found on a mature plant.

Bracts: Approximately 15–19 bi-colored red and white bracts subtend the cyathia.

Fully developed bracts are essentially ovate or elliptical with acuminate tips and acute bases. There is slight lobing on either side of the bract. Mature bracts measure about 15–19 cm long and about 10–11 cm wide. Texture is fairly smooth.

Growth habit: Cuttings root readily to produce a single stemmed cultivar which stands medium-tall and upright.

Growth rate: Cuttings root within about 12–18 days with occasional watering. Flowering occurs in about 9–11 weeks.

What is claimed is:

1. A new and distinct Poinsettia plant substantially as shown and described, characterized by a stable and uniform coloration of distinct red bracts with distinct white mottling.

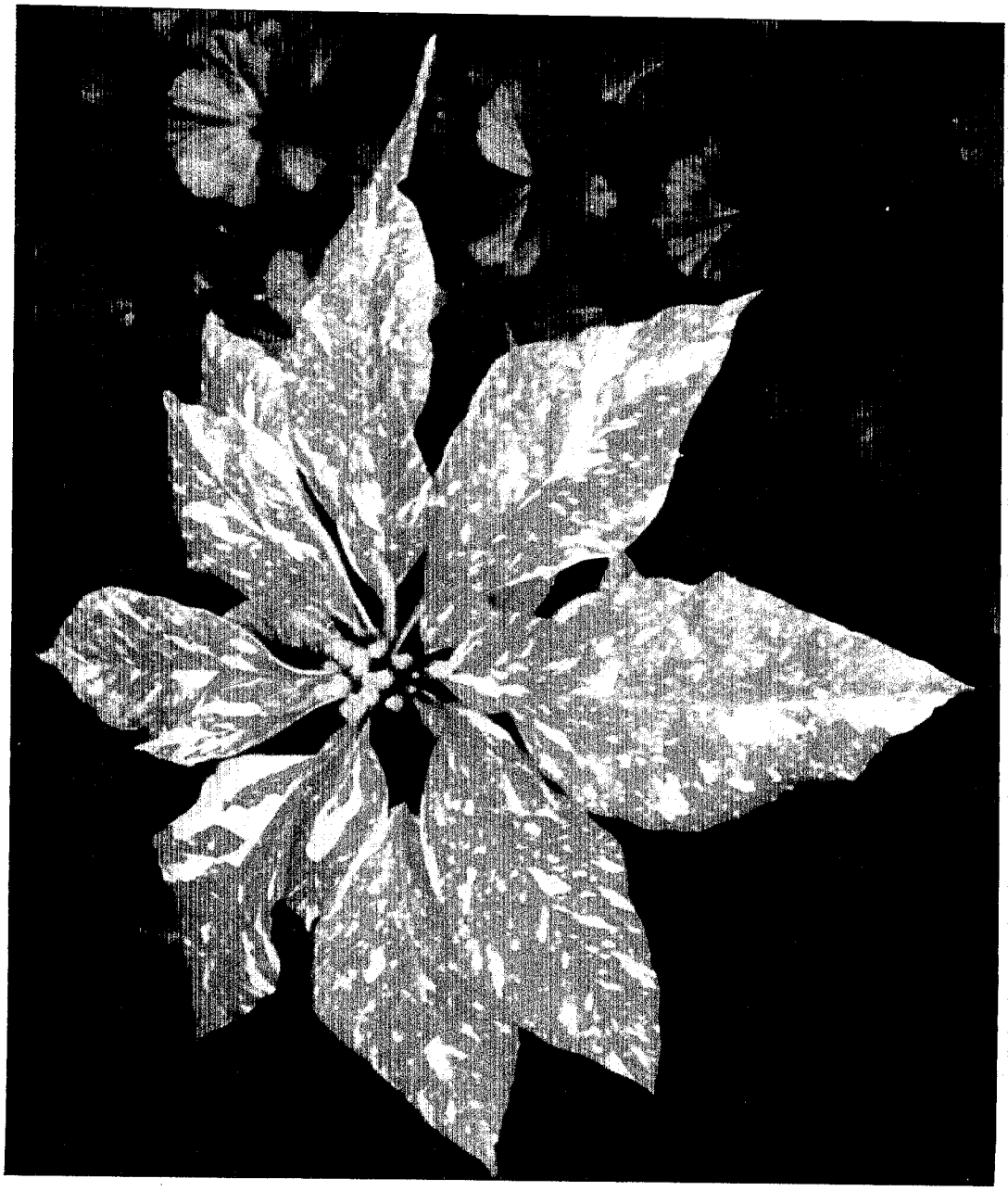

* * * * *